(12) United States Patent
Chung et al.

(10) Patent No.: US 6,790,954 B2
(45) Date of Patent: Sep. 14, 2004

(54) MUTANT ACTINOSYNNEMA PRETIOSUM STRAIN WITH INCREASED MAYTANSINOID PRODUCTION

(75) Inventors: Johnson Chung, Taipei (TW); Graham S. Byng, Snohomish, WA (US)

(73) Assignees: Immunogen, Inc., Cambridge, MA (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/057,561

(22) Filed: Jan. 29, 2002

(65) Prior Publication Data

US 2003/0157694 A1 Aug. 21, 2003

(51) Int. Cl.$^7$ .................... C07D 498/16; C07D 498/18; C12N 1/20; C12P 17/18
(52) U.S. Cl. ................. 540/462; 435/118; 435/119; 435/252.1; 435/253.2; 540/453; 540/456; 540/460; 540/463
(58) Field of Search ................. 435/252.1, 253.2, 435/119, 118; 540/453, 456, 460, 462, 463

(56) References Cited

U.S. PATENT DOCUMENTS 4,331,598 A * 5/1982 Hasegawa et al. .......... 435/119
4,450,234 A * 5/1984 Hasegawa et al. ....... 435/253.2

* cited by examiner

Primary Examiner—Herbert J. Lilling
(74) Attorney, Agent, or Firm—Sughrue Mion, PLLC

(57) ABSTRACT

A microorganism that is a mutant bacterial strain of the species *Actinosynnema pretiosum*, designated PF4-4, (ATCC PTA-3921), being capable of producing maytansinoid ansamitocins such as ansamitocin P-3 in improved yield compared to previous known strains, and capable of growth under varied culture conditions, and methods of producing maytansinoid ansamitocins by culturing PF4-4 in a suitable growth medium.

10 Claims, 3 Drawing Sheets

MUTANT ACTINOSYNNEMA PRETIOSUM STRAIN WITH INCREASED MAYTANSINOID PRODUCTION

BACKGROUND OF THE INVENTION

1. Field of the Invention

Figure 1:
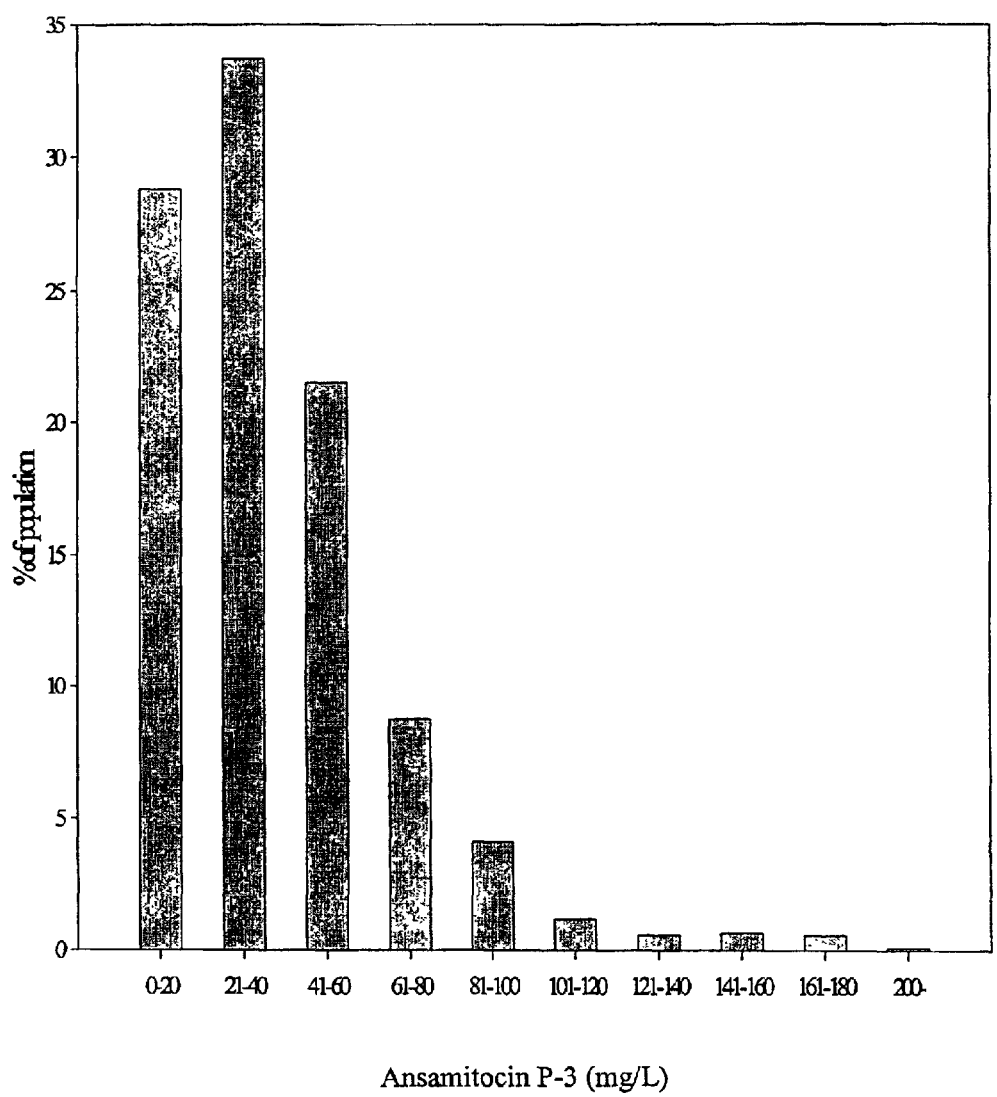

This invention relates to a microorganism that is a mutant bacterial strain of the species *Actinosynnema pretiosum*, designated strain PF4-4 (ATCC PTA-3921), being capable of producing maytansinoid ansamitocins such as ansamitocin P-3 in improved yield compared to previous known strains, and to methods of producing such maytansinoid ansamitocins from said strain PF4-4.

2. Background of the Invention

Bacteria of the species *Actinosynnema pretiosum* produce cytotoxic maytansinoid antibiotics (Higashide et al. *Nature* 270, 721–722, 1977). Bacteria of this species were originally classified and deposited as Nocardia sp., however subsequent characterization demonstrating the absence of any mycolic acids, cell wall type III/C (meso-diaminopimelic acid and no diagnostically important carbohydrates), a lack of sporangia, and the formation of motile elements, indicated that these strains are members of the genus Actinosynnema (Hasegawa, et al. "Motile Actinomycetes: *Actinosynnema pretosium* subsp. *pretosium* sp nov., subsp. nov., and *Actinosynnema pretosium* subsp. *auranticum* susp. nov." *Int. J. System. Bacteriol.* 33(2) :314–320, 1983).

The bacterially produced maytansinoids are called ansamitocins, and comprise a group of antitumor benzenoid ansamycin antibiotics that are distinguished from one another by their substitutions at the C-3 and C-14 positions, as shown by substituents R and $R_1$ of formula (I).

Several strains of Actinosynnema have been deposited, such as ATCC 31565, *Actinosynnema pretiosum* subsp. *auranticum*. The metabolic, physiological and maytansinoid-producing properties of ATCC 31565 are described in U.S. Pat. Nos. 4,331,598 and 4,450,234 to Hasegawa et al., issued on May 25, 1982, and May 22, 1984, respectively. ATCC 31565 is a gram-positive bacterium that is capable of growth on a wide range of carbon sources and which produces principally a mixture of maytansinoids and of C-14-hydroxymethyl substituted be harvested from the growth medium in low yield.

Maytansinoids were originally isolated from African plants (Kupchan et al. *J. Amer. Chem. Soc.* 94, 5294–5295, 1972). Production of maytansinoids from such sources was difficult because they were present in very small amounts. A maytansinoid-producing microorganism was subsequently isolated from sedge blades, which was classified as a new strain of the genus Nocardia, Nocardia sp. strain No.C-15003 (N-1). This strain was deposited as ATCC 31281, and is disclosed in U.S. Pat. No. 4,137,230 to Hashimoto et al., issued Jan. 30, 1979, and U.S. Pat. No. 4,162,940 to Higashide et al., issued Jul. 31, 1979. Purification of maytansinoids from this bacterium requires fewer steps and results in increased yield compared to purification from plant sources.

A second maytansinoid-producing strain was isolated from sedge blades, named Nocardia sp. Strain No. C-14482 (N-1001), deposited as ATCC 31309. This strain is disclosed in U.S. Pat. No. 4,292,309 to Higashide et al., issued Sep. 29, 1981.

A third strain was derived from ATCC 31309, designated C-14482, by a process of mutagenesis. This third strain was named Nocardia sp. No. N-1231, and was deposited as ATCC 31565. U.S. Pat. Nos. 4,331,598 to Hasegawa et al., issued May 25, 1982, and 4,450,234 to Hasegawa et al., issued May 22, 1984, disclose ATCC 31565.

All three of the above-mentioned Nocardia sp. strains produce maytansinoids called ansamitocins in small amounts. Thus, methods have been disclosed for the production of ansamitocin P-3 using Nocardia sp. Strain No.C-15003 (see, U.S. Pat. No. 4,356,265, to Hatano et al., issued Oct. 26, 1982; and Hatano et al. "Selective accumulation of ansamitocins P-2, P-3 and P-4, and biosynthetic origins of their acyl moieties" *Agric. Biol. Chem.* 48, 1721–1729, 1984). According to these methods, relatively small amounts of the desired product, ansamitocin P-3, are obtained, with yields of about 100 mg/L of fermentation broth.

Maytansinoids have potent cytotoxic activity and have demonstrated strong anti-tumor activity when delivered in conjugate form with a cell-binding agent. For example, U.S. Pat. No. 5,208,020 to Chari et al., issued May 4, 1993, discloses a cytotoxic agent comprising one or more maytansinoids linked to a cell targeting agent such as an antibody, whereby the maytansinoid is directed toward killing selected cell populations through the specific cell-binding agent. Likewise, U.S. Pat. No. 5,416,064, also to Chari at el., issued May 16, 1995, discloses new maytansinoids that are attached to cell-binding agents through cleavable disulfide linkages, whereby the maytansinoid is released intracellularly. These conjugates have pharmaceutical potential for the treatment of various cancers.

Because of the many therapeutic uses of maytansinoids, there exists a need for new strains of bacteria that are capable of producing ansamitocins in improved yield and in sufficient quantities to facilitate commercial development, for example, of such anti-cancer agents as described above and disclosed in U.S. Pat. Nos. 5,208,020 and 5,416,064. The present invention fulfills this need and more, as will be apparent to one of skill in the art upon reading the following disclosure and examples.

SUMMARY OF THE INVENTION

The present invention provides a bacterial strain, deposited as ATCC PTA-3921, also termed herein "PF4-4," that produces increased amounts of maytansinoids. PF4-4 was obtained by mutation from parent strain N-1231 (ATCC 31565) using ultraviolet light (UV light), 1-methyl-3-nitro-1-nitroso-guanidine (MNNG), and selection for enhanced maytansinoid production.

Thus, in a first embodiment, the invention comprises a mutated bacterial strain (PF4-4) of the species *Actinosynnema pretiosum* that produces much higher quantities of ansamitocins than the parental strain.

This embodiment of the invention is capable of producing more than 500 mg/L of ansamitocin P-3, which is a yield improvement of 5- to 10-fold compared to the parental strain.

This embodiment is further capable of producing substantial amounts of other ansamitocin species, for example ansamitocins P-2 and P-4. Furthermore, the relative amounts of specific ansamitocin species that are produced by this embodiment of the invention are capable of rational manipulation through the choice of carbon source used to support growth.

This embodiment is capable of growth upon a wide variety of carbon sources, and, with the exception of its capability to produce increased amounts of maytansinoids, is substantially similar to the parental strain (ATCC 31565) with respect to its morphology, physical and metabolic characteristics.

Thus, one object of the present invention is to provide a bacterial strain that is capable of enhanced maytansinoid production, whereby such maytansinoids are highly cytotoxic and can be used as therapeutic agents, for example in the form of a conjugate with a cell-specific component, in the treatment of many diseases, including cancer.

A second object of the invention is to provide a bacterial strain that is capable of enhanced maytansinoid production such that maytansinoid may be produced in sufficient quantities to facilitate commercial development of said therapeutic agents. to A third object is to provide a method for the production of maytansinoid ansamitocins from strain PF4-4 by culturing said strain in a growth medium comprising a suitable carbon source. The proportions of maytansinoid ansamitocins produced by this method may be predetermined by the choice of carbon source.

BRIEF DESCRIPTION OF THE DRAWINGS

FIG. 1 is a diagram showing the ansamitocin P-3 titer for 400 re-isolates from ATCC 31565.

FIG. 2 is a diagram showing one method for the production of ansamitocin P-3 by shake flask fermentation of *Actinosynnema pretiosum*, mutant strain PF4-4.

FIG. 3 is an HPLC chromatogram of a sample of broth extract from the fermentation of *Actinosynnema pretiosum*, mutant strain PF4-4.

DETAILED DESCRIPTION OF THE INVENTION

The present invention comprises a microorganism that is a mutant bacterial strain of the species *Actinosynnema pretiosum*, designated PF4-4 (ATCC PTA-3921), which is capable of producing maytansinoids, including ansamitocins such as ansamitocin P-3 and other ansamitocins in improved yields compared to previously known strains, including the parent strain (ATCC 31565).

The bacterial strain, PF4-4, of the present invention was produced from parent strain ATCC 31565 by mutation using UV light, 1-methyl-3-nitro-1-nitroso-guanidine (MNNG) and selection, to derive a strain of genetically altered bacteria that produces substantially higher quantities of maytansinoids than the parental strain. Thus, in fermentative growth, PF4-4 is capable of producing more than 500 mg/L of ansamitocin P-3, which is 5-10 fold more than the amount produced by the parental strain under the same conditions.

The *Actinosynnema pretiosum* strain of the present invention, herein PF4-4, was deposited under the provisions of the Budapest Treaty with the American Type Culture Collection, 10801 University Blvd., Manassas, Va. 20110-2209, on Dec. 11, 2001, and has been accorded Accession No. ATCC PTA-3921.

The parent strain ATCC 31565, from which the *Actinosynnema pretiosum* strain PF4-4 of the present invention is derived by mutation, is itself derived from *Actinosynnema pretiosum* strain ATCC 31309, as disclosed in U.S. Pat. No. 4,292,309, to Higashide et al., issued Sep. 29, 1981. As described above, bacteria of this species were originally classified and deposited as Nocardia sp., however subsequent characterization indicated that these strains are members of the genus Actinosynnema (Hasegawa, T. et al. "Motile Actinomycetes: *Actinosynnema pretosium* subsp. *pretosium* sp nov., subsp. nov., and *Actinosynnema pretosium* subsp. *auranticum* susp. nov." Int. J. System. Bacteriol. 33(2):314–320, 1983).

In the context of the present invention, the term "maytansinoid" refers to the class of highly cytotoxic drugs first isolated from the east African shrub *Maytenus ovatus*, and further includes: maytansinol and naturally occurring C-3 esters of maytansinol (U.S. Pat. No. 4,151,042); synthetic C-3 ester analogues of maytansinol (Kupchan et al., *J. Med. Chem.* 21:31–37, 1978; Higashide at al., *Nature* 270:721–722, 1977; Kawai et al., *Chem. Farm. Bull.* 32:3441–3451; and U.S. Pat. No. 5,416,064); C-3 esters of simple carboxylic acids (U.S. Pat. Nos. 4,248,870; 4,265,814; 4,308,268; 4,308,269; 4,309,428; 4,317,821; 4,322,348; and 4,331,598); and C-3 esters with derivatives of N-methyl-L-alanine (U.S. Pat. Nos. 4,137,230; 4,260,608; and Kawai et al., Chem. Pharm Bull. 12:3441, 1984).

In the context of the present invention, the term "ansamitocin" refers to various derivatives of ansainycin antibiotics (Hasegawa, T. et al. "Motile Actinomycetes: *Actinosynnema pretosium* subsp. *pretosium* sp nov., subsp. nov., and *Actinosynnema pretosium* subsp. *auranticum* susp. nov." *Int. J. System. Bacteriol.* 33(2):314–320, 1983; Tanida et al. "*Ansamitocin analogs from a mutant strain of nocardia. I. Isolation of the mutant, fermentation and antimicrobial properties.*" *J. Antibiotics* 34: 489–495, 1981) represented by the following general formula (I):

(I)

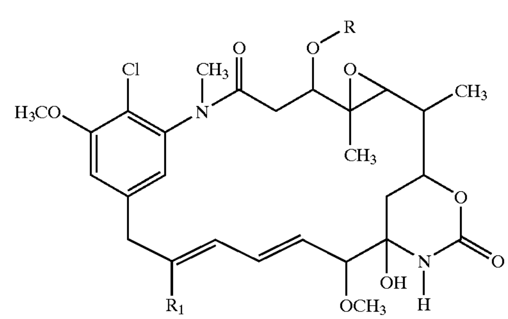

wherein R represents, for example, hydrogen, acetyl, propionyl, isobutyryl, butyryl, isovaleryl, and the like, and wherein $R_1$ represents, for example, methyl, hydroxymethyl, and the like.

Three major classes of ansamitocins are distinguished by different substituents on the ring structure: Ansamitocin P compounds with a methyl group at $R_1$ (C-14) in formula I; Ansamitocin PHM compounds with a hydroxymethyl group at $R_1$ (C-14) in formula I; and ansamitocin PDN compounds with a N-desmethyl ring structure and a methyl group at the $R_1$ position of formula I. In each class there are several members that are distinguished by different substituents R (C-3) in formula I. Originally, the ansamitocins with a methyl group at C-14 were isolated from Strain ATCC 31281, as described in U.S. Pat. No. 4,162,940.

Specifically, certain ansamitocins are designated herein by the abbreviations given as follows:

P-0 has R=hydrogen and $R_1$=methyl; also called maytansinol

P-1 has R=acetyl and $R_1$=methyl;

P-2 has R=propionyl and $R_1$=methyl;

P-3 has R=isobutyryl and $R_1$=methyl;

P-3' has R=butyryl and $R_1$=methyl;

P-4 has R=isovaleryl and $R_1$=methyl;

PHM-0 has R=hydrogen and $R_1$=hydroxymethyl;

PHM-1 has R=acetyl and $R_1$=hydroxymethyl;

PHM-2 has R=propionyl and $R_1$=hydroxymethyl;

PHM-3 has R=isobutyryl and $R_1$=hydroxymethyl;

PHM-3' has R=butyryl and $R_1$=hydroxymethyl;
PHM-4 has R=isovaleryl and $R_1$=hydroxymethyl;
PND-0 has N-desmethyl, R=hydrogen and $R_1$=methyl;
PND-1 has N-desmethyl, R=acetyl and $R_1$=methyl;
PND-2 has N-desmethyl, R=propionyl and $R_1$=methyl;
PND-3 has N-desmethyl, R=isobutyryl and $R_1$=methyl;
PND-3' has N-desmethyl, R=butyryl and $R_1$=methyl; and
PND-4 has N-desmethyl, R=isovaleryl and $R_1$=methyl.

The term "ansamitocin" further encompasses isomers thereof, including isomers occurring at the C-3, C-4, C-9 and C-10 positions.

(a) Biological Characteristics of *Actinosynnema pretiosum*, Mutant Strain PF4-4.

The morphological and metabolic characteristics of strain PF4-4 of the present invention are similar to those of the parental strain ATCC 31565, with the exception that strain PF4-4 exhibits enhanced maytansinoid production. The morphological and metabolic characteristics of the parent strain are disclosed in U.S. Pat. No. 4,450,234 to Hasegawa et al., issued May 22, 1984, and those portions describing said characteristics, including, but not limited to, columns 3-7 are hereby incorporated in their entireties by reference.

(b) Generation of *Actinosynnema pretiosum*, Mutant Strain PF4-4.

The PF4-4 strain is obtained from the parent strain N-1231, ATCC 31565, by the following procedure. The production of ansamitocin P-3 by N-1231 in FM4-1 medium is about 60 mg/L (average of n=400 experiments), as shown in Table 4, which shows ansamitocin P-3 production (mg/L) of the average of 400 colonies screened individually, and the three isolated colonies from strain N-1231, ATCC 31565, having the highest ansamitocin P-3 production in FM4-1 medium. Thus, in initial screening, strain N-1231, ATCC 31565, exhibits an average production of ansamitocin P-3 of 60 mg/L, and no colony exhibits production of greater than 221 mg/L.

TABLE 4

| Culture No. (number of experiments) | ATCC 31565 (n = 400) | 15–45 (n = 1) | 15–55 (n = 1) | 15–64 (n = 1) |
|---|---|---|---|---|
| HPLC Assay P-3 (mg/L) | 61 ρ 35 | 195 | 221 | 208 |
| Relative P-3 Titer | 1.00 | 3.19 | 3.62 | 3.41 |

Strain PF4-4 is preferably generated from ATCC 31565 in seven consecutive steps. These seven steps are: re-isolation; a first round of mutagenesis; re-isolation, preferably three times; UV mutagenesis, and MNNG mutagenesis.

These steps are performed according to standard procedures known to those of skill in the art, as described, for example, in Jeffrey Miller, 1992: A Short Course in Bacterial Genetics: A Laboratory Manual and Handbook for *Escherichia coli* and Related Bacteria, Cold Spring Laboratory Press, Woodbury, N.Y.

Re-isolation. Strain N-1231, ATCC 31565 is grown on agar plates in CM4-1 medium and two morphological phenotypes are observed: viz. yellow colonies and white colonies. Four hundred colonies of both types are re-isolated and their ansamitocin P-3 production is assayed. The ansamitocin P-3 titer distribution of the 400 colonies is shown in FIG. 1. The white colonies give consistently higher AP-3 titers than the yellow colonies. The titer comparison for strain N-1231, ATCC 31565, and the three colonies with the highest titers is shown in Table 4. Colony No. 15–55 exhibits the highest titer (221 mg/L) and is used in the subsequent step.

UV mutagenesis is described in detail in EXAMPLE 1 (below). In summary, spores from an 8-day old slant culture of colony No. 15–55 are collected in water and macerated on a vortex mixture. The number of colony forming units (cfu) is determined and is typically found to be about $2 \times 10^9$. Serially diluted samples containing varying numbers of cfu are then spread on agar plates and exposed to UV light from a germicidal lamp for different lengths of time. The killing rate for a 40 second exposure to such light is typically 99.9%. Plates treated for varying lengths of time are incubated at 28° C. for 5–7 days and then colonies are selected and analyzed for ansamitocin P-3 production. The colony having the highest ansamitocin P-3 production is selected for use in the next step.

MNNG mutagenesis is described in detail in EXAMPLE 2 (below). In summary, macerated spores are prepared as above, collected by centrifugation, and re-suspended in buffer containing 100 μg/mL MNNG. Preferably, the mutagenesis reaction is stopped after about 30 min by the addition of excess sodium thiosulfate and the bacteria are then collected by centrifugation, washed, and plated on agar plates for determination of the survival rate and for further analysis.

Table 5 shows the genealogy of strain PF4-4 and the production by intermediate isolates of ansamitocin P-3 (mg/L) as assayed by HPLC (see EXAMPLE 6). The media used in Table 5 are given in Table 6A. Within Table 5, the entry "d/n" represents the time of fermentation in days (d) and the number of cultures tested (n).

TABLE 5

| Medium | → ATCC 31565 | → re-i 15-55 | → UV 48-315 | → re-i 77-72 | → re-i 106-26 | → re-i 128-18 | → UV 15-447 | MNNG PF 4-4 |
|---|---|---|---|---|---|---|---|---|
| FM 27-44 | 55 ρ 16 (n = 30) | 143 ρ 15 (8 d/n = 10) | 220 (8 d/n = 1) | | | | | |
| FM 112-37 | 48 ρ 15 (n = 10) | | | | 331 ρ 24 (8 d/n = 5) | 382 (8 d/n = 1) | | |
| FM 112-37 | 49 ρ 14 (n = 10) | | | | 305 ρ 13 (8 d/n = 10) | 435 (8 d/n = 1) | | |
| FM 4-4 | 64 ρ 26 (n = 5) | | | | | | 153 (6 d/n = 1) | 268 (6 d/n = 1) |
| FM 4-7 | 152 ρ 33 (n = 6) | | | | | 325 ρ 12 (6 d/n = 6) | | 401 ρ 8 (6 d/n = 6) |
| FM 4-6 | 187 ρ 24 (n = 5) | | | | | | | 369 ρ 16 6 d/n = 4) |

(c) Production of Maytansinoids from *Actinosynnema pretiosum* Strain PF4-4.

Growth of the bacterial strain PF4-4 is performed under controlled conditions and can employ a wide variety of media and conditions. For example, PF4-4 can be grown under similar conditions and with similar media to those described for ATCC 31565 or ATCC 31281 in issued U.S. Pat. Nos. 4,137,230; 4,162,940; 4,331,598; 4,356,265; 4,450,234; and as described in Hatano et al., *Agric. Biol. Chem.* 48, 1721–1729, 1984. Thus, the strain PF4-4 tolerates a wide variety of carbon sources, which also support fermentative production of maytansanoids. Exemplary growth media are given in Tables 6A and 6B. Table 6A shows media that support growth of PF4-4 and which are utilized in Table 5. Table 6B shows further media suitable for the propagation and/or growth of PF4-4.

Figure 2:
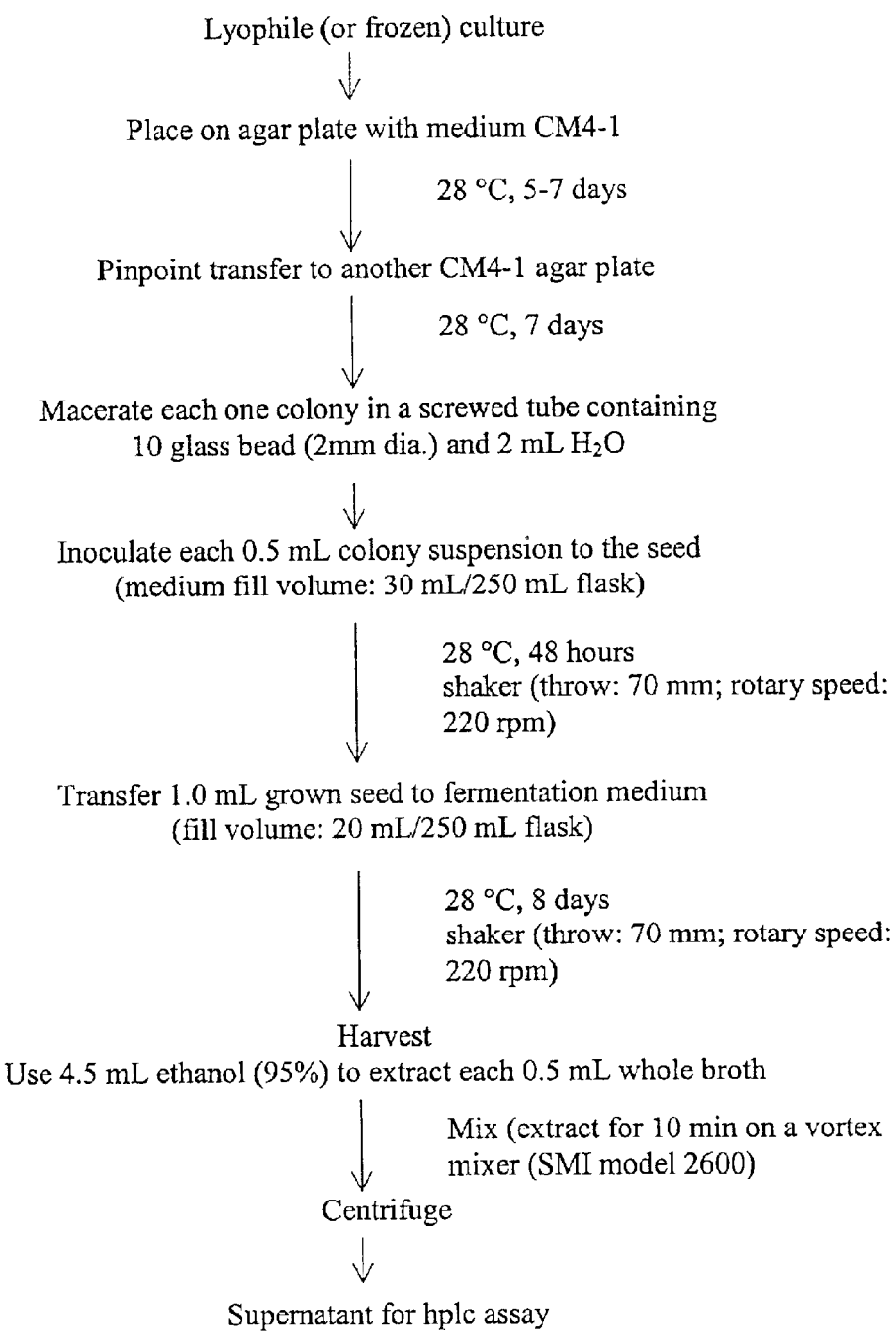

One preferred method for fermentative production of maytansanoids from strain PF4-4 is represented in the flowchart of FIG. 2 and is further described in EXAMPLE 3 (below).

TABLE 6A

Composition entries are % (w/v). Sterilization was 121° C. for 20 minutes. [1]Added last.

|  | FM 27-44 | FM 112-37 | FM 4-4 | FM 4-6 | FM 4-7 |
|---|---|---|---|---|---|
| Dextrin (Lodex-5) | 6 | 6 | 5 | 5 | 5 |
| Maltose (Difco) | 4 | 4 | 2 | 2 | 2 |
| Proflo (Traders) |  |  | 2.0 | 2.5 | 2.75 |
| Soybean Flour (ADM) | 1.5 | 2.0 |  |  |  |
| Pharmamedia (Traders) | 0.5 |  |  |  |  |
| CSP (Roquette) | 0.5 | 0.5 | 0.5 | 0.15 | 0.15 |
| P. Dry Yeast (Difco) | 0.25 |  |  |  |  |
| $MgSO_4 \cdot 7H_2O$ (Wako) | 0.05 |  |  |  |  |
| $CaCO_3$ (Hayashi) |  |  | 0.5 | 0.5 | 0.6 |
| $(NH_4)_2SO_4$ (Wako) |  | 0.05 |  |  |  |
| $KH_2PO_4$ (Wako) | 0.05 | 0.04 |  |  |  |
| $K_2HPO_4$ (Wako) |  | 0.05 | 0.06 | 0.06 | 0.06 |
| $CaCl_2 \cdot 2H_2O$ (Wako) | 0.5 | 0.5 |  |  |  |
| $NaHCO_3$ (Wako) |  | 0.2 |  |  |  |
| Zeolite | 0.1 |  |  |  |  |
| $FeSO_4 \cdot 7H_2O$ (Wako) | 0.0002 | 0.0002 | 0.0002 | 0.0002 | 0.0002 |
| $ZnSO_4 \cdot 7H_2O$ | 0.0002 |  |  |  |  |
| $CoCl_2 \cdot 6H_2O$ (Baker) | 0.001 |  |  | 0.0005 | 0.0005 |
| Nicotinic Acid | 0.0002 |  |  |  |  |
| $MnSO_4 \cdot H_2O$ | 0.0002 |  |  |  |  |
| Isobutanol[1] (Tedoa) | 0.1 | 0.5 | 0.5 | 0.3 | 0.3 |
| SAG471 (Witco) |  | 0 | 0.06 | 0.04 | 0.04 |
| pH | 6.8 | 6.8 | 6.8 | 7.2 | 7.35 |

TABLE 6B

Related Media

|  | (%, w/v) |
|---|---|
| Slant and plate culture, CM4-1 Agar |  |
| Yeast extract (Difco) | 0.3 |
| Malt extract (Difco) | 0.3 |
| Soytone (Difco) | 0.5 |
| Glycerol (Difco) | 1.0 |
| Bacto Agar (Difco) | 2.0 |
| Adjust pH to 6.5 before sterilization |  |
| Sterilization: 121° C., 20 minutes |  |

TABLE 6B-continued

Related Media

|  | (%, w/v) |
|---|---|
| Seed Medium, VM4-1 |  |
| Soluble starch (BDH) | 2.0 |
| Glucose (Shuling) | 1.0 |
| Soybean meal (ADM) | 1.0 |
| CSP (Roquette) | 0.5 |
| Soytone (Difco) | 0.5 |
| NaCl (Wako) | 0.3 |
| $CaCO_3$ (Hayashi) | 0.5 |
| pH: 6.8 |  |
| Sterilization: 121° C., 20 minutes |  |

Analysis of Ansamitocins

In U.S. Pat. Nos. 4,331,598 and 4,450,234, the parental strain ATCC 31565 is disclosed as producing two classes of ansamitocins that are distinguished by the presence of a methyl or hydroxymethyl group at C-14 (see formula I). For both classes, several different ansamitocins are produced that differ in their respective acyl side chain bound to the C-3 hydroxyl group, and with respect to whether C-14 carries a methyl or hydroxymethyl group (or, in subsequent studies, N-desmethyl). The nomenclature used herein for the permuted compounds is defined above with reference to formula (I).

Ansamitocin P-3 is the major product of PF4-4 and the parental strain ATCC 31565, under certain growth conditions. If the bacteria are grown in the presence of valine or isobutyric acid (see U.S. Pat. No. 4,228,239) or isobutyl alcohol or isobutylaldehyde (see U.S. Pat. No. 4,356,265) other ansamitocin compounds are present in minor amounts.

When PF4-4 strain is grown in different fermentation media (designated FM in Table 6), which all contain isobutyl alcohol, ansamitocin P-3 is the predominant ansamitocin produced. Fermentation broths are diluted with ethanol or acetonitrile, vortexed, then centrifuged and the supernatant assayed for ansamitocin P-3 content.

Ansatomycins are preferably fractionated and analyzed by reverse phase high performance liquid chromatography (hplc), but any suitable technique, such as, for example, MALDI-TOF or thin-layer chromatography may be used. In one method employing HPLC, fermentation broths are extracted with organic solvents, such as ethyl acetate, methylene chloride or chloroform, and the content of P-3 in the organic solvent is determined by reverse phase hplc as described in EXAMPLE 6.

EXAMPLES

The invention will now be illustrated by reference to non-limiting examples.

Example 1

UV Mutagenesis

Spores from an 8-day old slant preparation of colony No. 15–55 were collected by washing the slant [slant size: 2.3×18 cm tube filled with 16–18 mL of CM4-1 agar (for composition see Table 6b)] with 10 mL of water. Five mL of the water with the suspended spores were placed in a screw cap tube (size: 1.1×11 cm) containing 10 glass beads of 2.0 mm diameter for maceration. The tube was vortexed for five minutes and the macerated spore suspension was then serially diluted into a 0.1% aqueous Tween 60 solution at $10^3$, $10^4$, and $10^5$-fold dilutions. (The macerated suspension-typically contains $2 \times 10^9$ cfu.) From each dilution, 0.1 mL of the suspension was plated on a CM4-1 agar plate (9.5 cm diameter), which was exposed to a suitable germicidal UV light source: the open agar plate was placed under a 15 W germicidal lamp at about 20 cm distance and exposed for 20–40 seconds to the UV light. (The killing rate for a 40 second exposure was about 99.9%.) The exposed plates were cultivated at 28° C. for 5–7 days, and single colonies were then transferred to another CM4-1 agar plate and grown in grids of 16 colonies per plate. Colonies were then chosen for further evaluation.

Example 2

MNNG Mutagenesis

Spores from an 8-day old slant preparation were collected by washing the slant (slant size: 2.3×18 cm tube filled with 16–18 mL of CM4-1 agar) with 10 mL of water. Five mL of the water with the suspended spores were placed in a screw cap tube (size: 1.1×11 cm) containing 10 glass beads of 2.0 mm diameter for maceration. The tube was vortexed for five minutes and the spores were collected by centrifugation at 2100×g for 15 min. The supernatant was discarded and the pellet was resuspended in 4 mL of sterile 0.05 M tris maleic acid buffer, pH 8.0 containing (w/v) 0.1% ammonium sulfate, 0.01% magnesium sulfate hepta-hydrate, 0.005% calcium chloride dihydrate, 0.00025% ferrous sulfate hepta-hydrate, and 100 µg/mL of MNNG. The suspension was vortexed for 30 min, then the reaction was stopped by the addition of 3 mL of a saturated sodium thiosulfate solution. The spores were collected by centrifugation, then resuspended in 5 mL of water. This suspension was used for selection and an appropriate dilution was smeared on a CM4-1 agar plate to determine the survival rate.

Example 3

Shake Flask Fermentation to Produce Ansamitocin from PF4-4.

A stored PF4-4 culture, for example a lyophilized or frozen culture, was grown on CM4-1 agar plates at 28° C. for 5–7 days. Single colonies were then transferred to a second, gridded CM4-1 agar plate, (typically 16 colonies were transferred to a plate of 9.5 cm diameter), and the plate was incubated at 28° C. for 7 days, during which period colonies of 6–15 mm in diameter grew. A single colony was then macerated by vortexing for 10 minutes in a closed tube containing ten 2-mm-diameter glass beads and 2 mL of water. Part of the colony suspension (0.5 mL) was then transferred to a 250 mL culture flask containing 30 mL seed medium, VM4-1 (for composition, see Table 6b). The seed flask was incubated on a rotary shaker (220 rpm, 70 mm throw) at 28° C. for 48 hours, after which 1 mL of the seed growth suspension was transferred to a 250 mL culture flask containing 20 mL of fermentation medium FM4-4. The fermentation flask was incubated under the same conditions as the seed flask for 6 days, after which ansamitocin production was assayed as described in EXAMPLE 5 and was found to be 268 mg/L.

Different fermentation broths can be used. Examples of preferred broths and the corresponding levels of ansamitocin P-3 production obtained are listed in Table 5 and the compositions of the broths are shown in Table 6a.

Example 4

Preparation of Frozen PF4-4 Cultures for Long-Term Storage.

A macerated colony suspension in 2 mL of water was prepared as described in EXAMPLE 3, then 0.2 mL of the suspension was inoculated onto a slant culture (slant size: 2.3×18 cm tube filled with 16–18 mL of CM4-1 agar) and incubated at 28° C. for 7 days. The slant was washed out with 10 mL of cryogen solution (10% glycerol and 5% lactose in water), which was then subjected to the maceration procedure described above. The macerated suspension was aliquoted (1.5 mL) into cryovials and frozen at 75° C. or in liquid nitrogen.

Example 5

Preparation of Lyophilized PF4-4 Bacteria for Long-Term Storage.

An 8-day old slant culture (slant size: 2.3×18 cm tube filled with 16–18 mL of CM4-1 agar) was scraped into 3 mL of skimmed milk solution (5% (w/v) skimmed milk powder in water). The suspension was then macerated in a closed tube containing ten 2 mm diameter glass beads by vortexing for 5 min. Aliquots of 0.5 mL were distributed into vials and lyophilized. Each vial preferably contained about $1.2 \times 10^8$ cfu.

Example 6

Analysis of Ansamitocin P-3 in Fermentation Broth

Figure 3:
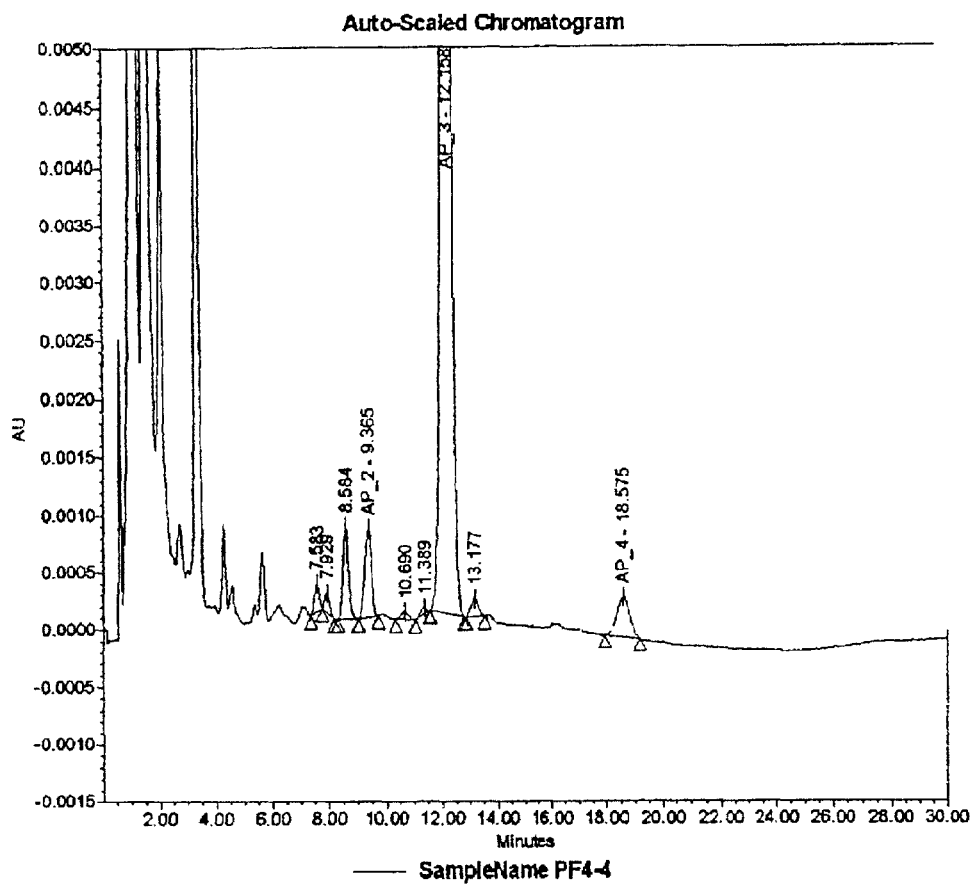

Fermentation broth (0.25 mL) was transferred to a screw cap tube containing ethanol (4.75 mL). (Alternatively, 0.25 mL of whole fermentation broth was mixed with 2.25 mL of ethanol.) The solution was vortexed for ten minutes, then centrifuged at 2100×g for ten minutes. The supernatant was removed and subjected to reverse phase hplc analysis. Preferably, a Symmetry Shield C8 column (3.6×150 mm) was used. The mobile phase was preferably water/acetonitrile/methanol at a ratio (v/v) of 55/35/10 and was preferably used at a flow rate of 1.0 mL/min. Chromatography was monitored by measuring UV absorption at 252 nm. A typical hplc trace of a broth extract is shown in FIG. 3, in which ansamitocin P-3 elutes at about 12.2 minutes after the injection.

Certain patents and printed publications have been cited in the foregoing disclosure, which are hereby incorporated in their respective entireties by reference.

While the invention has been described in detail and with reference to specific embodiments thereof, it will be apparent to one of skill in the art that various changes and modifications can be made without departing from the spirit and scope of the invention. Therefore the scope of the present invention is intended to be limited only by the scope of the following claims.

What is claimed is:

1. *Actinosynnema pretiosum* strain PF4-4 having ATCC accession number PTA-3921.

2. An enhanced *Actinosynnema pretiosum* strain that produces an ansamitocin in an amount of between about 1.2-fold and about 10-fold more than the amount produced by *Actinosynnema pretiosum* strain N-1231 (ATCC accession number 31565), said enhanced *Actinosynnema pretiosum* strain produced by a method comnrising:
   (a) treating a bacterial culture of *Actinosynnema pretiosum* with a mutagen,
   (b) growing the treated bacterial culture of (a) under selective pressure, (c) selecting an isolate from the product of (b) that exhibits increased production of an ansamitocin compared with the culture used in (a), and (d) optionally repeating (a), (b) and (c) until an isolate that produces between about 1.2-fold and about 10-fold more of an ansamitocin than *Actinosynnema pretiosum* strain N-1231 is obtained.

3. The enhanced *Actinosynnema pretiosum* strain according to claim 2, wherein the enhanced strain produces an ansarnitocin in an amount of between 1.2-fold and 10-fold more than the amount produced by *Actinosynnema pretiosum* strain N-1231 (ATCC accession number 31565).

4. The enhanced *Actinosynnema preliosum* strain according to claim 2, wherein the enhanced strain produces an ansainitocin in an amount of between 1.8-fold and 10-fold more than the amount produced by *Actinosynnema pretiosum* strain N-1231 (ATCC accession number 31565).

5. The enhanced *Actinosynnema pretiosum* strain according to claim 2, wherein the enhanced strain produces an ansamitocin in an amount of between 5-fold and 10-fold more than the amount produced by *Actinosynnema pretiosum* strain N-1231 (ATCC accession number 31565).

6. The enhanced *Actinosynnema pretiosum* strain according to claim 2, wherein the ansamitocin is ansamitocin P-3.

7. A method for producing an ansamitocin, which comprises cultivating the enhanced *Actinosynnema pretiosum* strain of claim 2 in a culture medium comprising a suitable carbon source.

8. The method of claim 7, wherein said ansamitocin is one or more ansamitocins of formula (I) or isomers thereof:

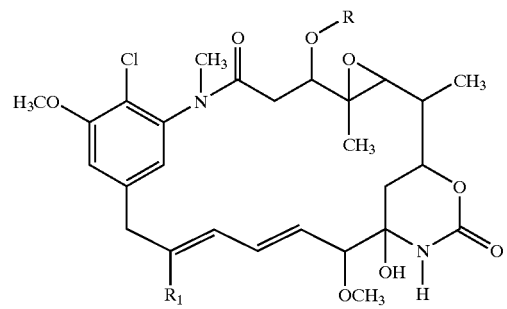

(I)

wherein R is selected from the group consisting of hydrogen, acetyl, propionyl, isobutyryl, butyryl, and isovaleryl, and $R_1$ is selected from the group consisting of methyl and hydroxymethyl.

9. The method of claim 8, wherein R is isobutyryl and $R_1$ is methyl.

10. The method of claim 7, wherein said ansamitocin is ansamitocin P-3 and said carbon source comprises one or more carbon sources selected from the group consisting of valine, isobutyric acid, isobutyl alcohol, and isobutylaldehyde.

* * * * *